United States Patent [19]

Peters

[11] E Patent Number: Re. 33,395

[45] Reissued Date of Patent: Oct. 23, 1990

[54] ANKLE BRACE

[76] Inventor: Rick E. Peters, 1436 Hepburn Ave. Apt. 1, Louisville, Ky. 40204

[21] Appl. No.: 383,974

[22] Filed: Jul. 17, 1989

Related U.S. Patent Documents

Reissue of:

[64] Patent No.: 4,510,927
Issued: Apr. 16, 1985
Appl. No.: 484,880
Filed: Apr. 14, 1983

[51] Int. Cl.[5] ..... A61F 3/00
[52] U.S. Cl. ..... 128/80 H
[58] Field of Search ..... 128/80 R, 80 F, 80 H, 128/87 R, 88, 165, 166

[56] References Cited

U.S. PATENT DOCUMENTS

| | | | |
|---|---|---|---|
| Re. 15,466 | 9/1922 | Hamilton | 128/80 |
| 112,952 | 3/1871 | Nisewander | 128/80 |
| 830,894 | 9/1906 | Garrod | 128/80 |
| 3,506,000 | 4/1970 | Baker | 128/80 |
| 3,674,023 | 7/1972 | Mann | 128/80 |
| 3,955,565 | 5/1976 | Johnson, Jr. | 128/80 |
| 4,133,311 | 1/1979 | Karczewski | 128/80 |
| 4,166,460 | 9/1979 | Applegate | 128/80 |
| 4,280,489 | 7/1981 | Johnson, Jr. | 128/80 |
| 4,287,920 | 9/1981 | Johnson, Jr. | 128/80 |
| 4,320,748 | 3/1982 | Racette et al. | 128/80 |

*Primary Examiner*—John D. Yasko
*Attorney, Agent, or Firm*—Woodard, Emhardt, Naughton Moriarty & McNett

[57] ABSTRACT

An ankle brace which permits plantoflexion and dorsiflexion while limiting inversion and eversion of the ankle. The brace includes a heel stirrup including a heel portion received under the wearer's heel, and upstanding inner and outer side portions which extend along and over the medial malleolus and the lateral malleolus. A pair of padded members are securable to the lower part of the person's leg and are pivotally attached to the inner and outer side portions of the stirrup with the points of pivotal movement being located at the position of the medial malleolus and the lateral malleolus. A VELCRO strap is also used to secure the stirrup to the person's foot.

14 Claims, 2 Drawing Sheets

ANKLE BRACE

Matter enclosed in heavy brackets [ ] appears in the original patent but forms no part of this reissue specification; matter printed in italics indicates the additions made by reissue.

BACKGROUND OF THE INVENTION

*This application is a reissue of Ser. No. 484,880 filed Apr. 14, 1983 now U.S. Pat. No. 4,510,927.*

1. Field of the Invention

The present invention relates to the field of ankle braces, and in particular to an ankle brace which immobilizes the ankle against inversion or eversion while permitting plantoflexion and dorsiflexion.

2. Description of the Prior Art

The ankle is a part of the body which is one of the most prone to injury. Once an ankle injury has occurred, it is usually necessary or desirable to immobilize the ankle in a manner to permit healing of the ankle. Various approaches have been proposed in the prior art to support the ankle during the healing process, as well as for other purposes including to prevent further injury.

Among athletes, injuries of the ankle such as by ankle sprains may be second in frequency only to injuries to the knee. In a recent survey of injuries suffered by various college football teams during 1982, injuries of the ankle were second in occurrence only to knee injuries. Of 2761 injuries to the athletes surveyed. 469 or 16% of the injuries were of the ankle, as compared to 21% of the injuries having occurred to the knee. Of course, the freguency of ankle injuries will vary among the different teams and sports. Also, injuries to the ankle occur in a variety of setting in addition to athletic endeavors. The important point is that injuries to the ankle are common, and there is therefore a significant concern for protecting the ankle during recovery and against further injury.

Considerable disagreement currently exists as to the advisability and actual effectiveness of using tape in the treatment or prevention of ankle injuries. Adhesive tape has been used by persons including many trained professionals, for protecting the ankle, although many disadvantages appear to exist. The application of tape requires the time of a trained person, and is expensive both in requiring the use of trained personnel and in the cost of the tape itself. The support afforded by the tape may reduce by 40% after ten minutes of vigorous activity. Repeated use of ankle taping may lead to irritation to the bare, movable skin to which it is applied. Also, moisture collecting under the tape will cause the tape to loosen, thus diminishing its effectiveness.

Perhaps of equal concern in the usage of adhesive tape is that the presence of the tape can lead to a weakening of the ankle, particularly the supporting muscle tendons. The taping often replaces the practice of thoroughly exercising the ankle joint, and may give the person a false security which eventually becomes a psychological crutch. Moreover, the rigid taping of the ankle locks the subtalar joint, thereby increasing stress to the knee joint.

Another alternative for the protection of the ankle is the use of ankle wraps, such as elastic bandages. However, the use of such bandages carries many of the same disadvantages as described with respect to adhesive tape. In addition, such wraps may loosen considerably, perhaps in the range of 34–77%, thus reducing the effectiveness of the wrap for the intended purpose of protecting the ankle. An elastic wrap designed particularly for supporting the ankle is described in U.S. Pat. No. 3,506,000, issued to Baker on Apr. 4, 1970. Another device constructed for this purpose is described in U.S. Pat. No. 3,674,023, issued to Mann on July 4, 1972. The Mann device comprises a heel boot shaped much like the rear half of a boot and mounted onto the foot by straps utilizing VELCRO strips for attachment. An additional, informative discussion of the prior art in this field is also included in the Mann patent.

A third alternative that has surfaced in the prior art is the employment of reusable ankle braces. Such braces have the advantage of being able to be used many times, thus minimizing the cost factor. Also, some of the disadvantages of adhesive tape or elastic bandages are overcome by these braces. However, prior art braces have typically involved only minimum of consideration to the anatomical structure and functioning of the ankle. As a result, many braces act to diminish or eliminate certain types of movement of the ankle while the braces are in use. Many of the prior art braces have also been quite bulky and uncomfortable, and in certain instances have not done an effective job of protecting the ankle as desired.

There are currently two types of ankle braces that are prevalent in the market. A first type is the lace-up variety such as that available from Tru-Fit Marketing Corporation, 680 Lynnway, Lynn, Mass. 01905. The Tru-Fit ankle support is made of vinyl with nylon reinforced webbing and extends from the instep to above the ankle. The support laces up the front much like a high top boot or shoe. A similar type of ankle support is disclosed in U.S. Pat. No. 4,280,488, issued to Polsky on July 28, 1981.

An ankle supporter is discussed in U.S. Pat. No. 15,446, issued to Hamilton on June 17, 1922. The Hamilton supporter includes side members made of leather, felt, woven fabric or other suitable material having flexibility to permit the sides to be pulled over the ankle portions from the rear of the ankle at which the sides are integrally joined. The side members include padding to provide support for the narrower portions of the ankle structure, and the whole unit is secured to the ankle by lacing over the front of the foot. A similar device which is strapped onto the foot and wraps over the sides of the ankle from the rear is disclosed in U.S. Pat. No. 4,133,311, issued to Karczewski on Jan. 9, 1979.

A second type of brace which is currently common in the market is available from Aircast Incorporated of Summit, N.J. This brace may be covered by any of U.S. Pat. Nos. 3,955,565, 4,280,489 and 4,287,920. The Aircast brace includes a bottom pad and a pair of upwardly extending side members which are secured to either side of the ankle by VELCRO strips which wrap around the ankle or leg. The Aircast design is fairly simple, and apparently relies on the vertically extending pads to protect the ankle from inversion and eversion. However, the brace is relatively bulky and therefore may not be useful with certain types of footwear, particularly with high top shoes. Also, the Aircast brace includes a pivot point at the connection of the bottom pad with the side members, thus providing for pivoting at an anatomically incorrect location at the bottom of the foot. This leads to a restriction of dorsiflexion and plantoflexion of the ankle.

A simplified ankle brace is described in U.S. Pat. No. 112,952, issued to Niswander on Mar. 21, 1871. The Niswander ankle brace includes a stirrup formed of sheet metal and configured to extend under the foot at about the heel. The stirrup curves upwardly a short distance along the inside of the foot, and on the outside extends upwardly to above the ankle bone. A side plate which is laced to the lower part of the leg is connected with the side plate by a rivet, thereby allowing for pivoting motion of the side plate relative the stirrup.

An ankle brace and supporter is shown in U.S. Pat. No. 830,894, issued to Garrod on Sept. 11, 1906. The Garrod device includes pairs of longitudinal members positioned on each side of the leg and pivotally mounted to a plate received under the heel of the foot. The longitudinal members are strapped to the leg. As with certain other devices, the pivoting motion permitted by this device is inappropriate to the ankle structure since the pivot is positioned below the foot.

SUMMARY OF THE INVENTION

Briefly describing one aspect of the present invention there is provided an ankle brace for inhibiting eversion and inversion of the ankle while permitting plantoflexion and dorsiflexion. The invention includes a heel stirrup having upwardly extending side portions which are pivotally connected to inner and outer padded members received againt the person's leg. The axes for pivoting of the side portions relative the padded members are locate adjacent the respective inner and outer ankle bones.

It is an object of the present invention to provide a reusable brace that protects the ankle against inversion and eversion injuries, and which provides protection for the ankle during recovery from such injuries.

Another object of the present invention is to provide an ankle brace which is easily put on and taken off, and which requires no assistance from trained personnel.

A further object of the present invention is to provide an ankle brace which is lightweight and comfortable for prolonged use, and which also provides a maximum of protection for the ankle.

It is another object of the present invention to provide an ankle brace which is relatively low in cost as compared to alternative ankle protections, and which also avoids disadvantages of certain prior art devices intended for protecting the ankle.

A further object of the present invention is to provide an ankle brace which affords additional lateral support for the major type of ankle sprain to the lateral side, and which also permits total plantoflexion and dorsiflexion needed in walking and running.

Further objects and advantages of the present invention will become apparent from the description of the preferred embodiment which follows.

DESCRIPTION OF THE PREFERRED EMBODIMENT

Figure 1:
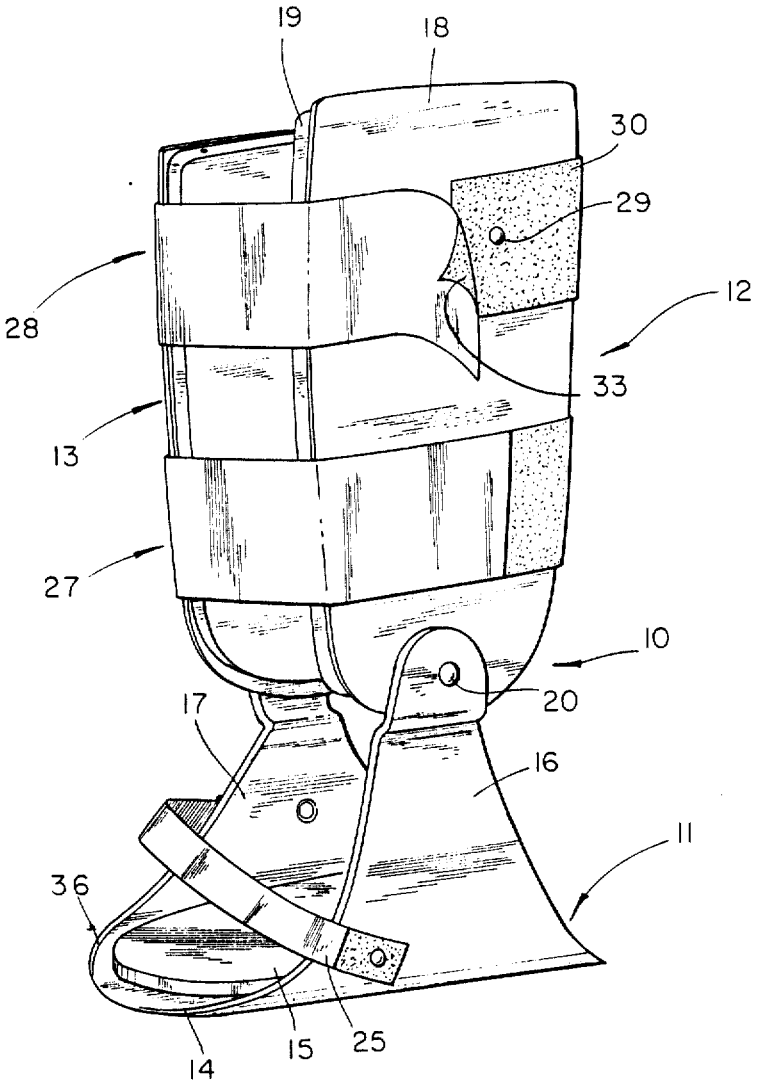
FIG. 1 is a perspective view of an ankle brace constructed in accordance with the present invention.
Figure 2:
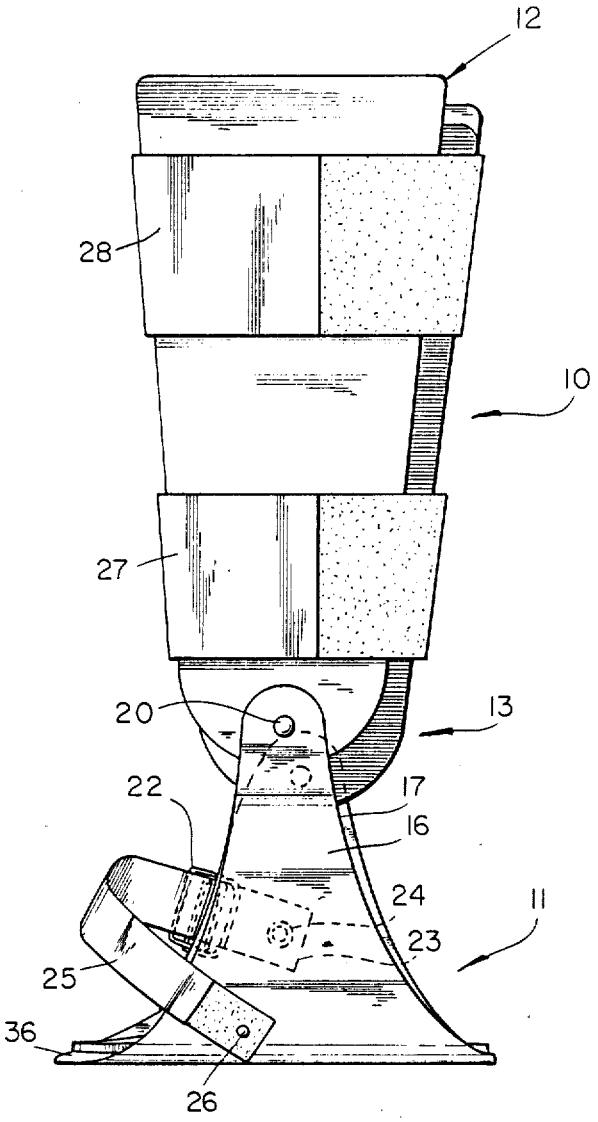
FIG. 2 is a side, elevational view of the ankle brace of FIG. 1.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

An individual's ankle has four movement referred to as plantoflexion, dorsiflexion, inversion and eversion. Dorsiflexion and plantoflexion are the up and down movement of the foot. These movements initiate from the talotibial joint and are used mainly in walking and running. This joint movement is left unrestricted by the ankle brace of the present invention. Inversion and eversion are the inward and outward turning of the ankle. These two movements initiate from the talocalcaneal joint and are the main causes of ankle injuries. The present invention provides an ankle brace which restricts these types of movement.

Referring in particular to the drawings, there is shown an ankle brace 10 constructed in accordance with the preferred embodiment. The ankle brace 10 includes a heel stirrup 11 mounted to a pair of padded members 12 and 13. As will be apparent from the following description, the ankle brace provided hereby permits plantoflexion and dorsiflexion of the ankle, while protecting the ankle from eversion and inversion.

The heel stirrup 11 includes heel portion 14 which is sized and configured to be conveniently received below and adjacent the heel of the use of the brace. The heel portion may include a heel pad 15 to provide additional comfort for the wearer. The stirrup also includes a pair of upstanding inner and outer side portions, 16 and 17 respectively. The side portions are configured to be received adjacent the ankle of the wearer, particularly extending upwardly along opposite sides of the ankle and overlying the ankle bones.

As used herein, the ankle bones of relevance to the present invention are in fact portions of the tibia and the fibula. The inner ankle bone is considered for purposes herein to refer to the medial malleolus, and the outer ankle bone refers to the lateral malleolus. Although these are portions of the tibia and the fibula, respectively, they are the prominent bone structure protruding laterally in the area of the ankle and may be considered ankle bones as relates to the present invention.

The inner and outer padded members, 12 and 13 respectively, are similarly configured and constructed. In the preferred embodiment, the padded members comprise a substantially rigid support member, such as 18, to which is secured padding, such as 19. The inner padded member 12 is pivotally connected with the inner side portion 16 of the heel stirrup and is configured to be received adjacent the inside of the lower portion of the person's leg. Similarly, the outer padded member 13 is pivotally connected with the outer side portion 17 of the heel stirrup and is configured to be received adjacent the outside of the lower portion of the person's leg.

The ankle brace 10 provides for pivotal connection of the respective side portions and padded members to locate the pivoting axes adjacent the respective ankle bones. The pivoting connection may be afforded by a variety of constructions, but preferably includes rivets 20 and 21 which attach together the associated side portions and padded members. The inside rivet 20 is positioned to be adjacent the medial malleolus such that the axis of pivoting extends through the medial malleolus. Similarly, the outside rivet 21 is positioned to be adjacent the lateral malleolus such that the axis of pivoting extends through the lateral malleolus. Consequently, the outer rivet is positioned lower than and rearward of the inside rivet to correspond with the related positioning of the medial malleolus and the lateral malleolus.

Means are provided for attaching the heel stirrup to the user's foot. This means preferably includes a strap connectable between the side portions of the stirrup. In the preferred embodiment, there is provided a buckle 22 attached through strap 23 and rivet 24 to the outer side portion 17 of the stirrup. A second strap 25 is secured to the inner side portion 16 by means of a rivet 26.

Although various types of straps and buckles may be used, it is preferred to employ VELCRO straps in the following manner. The strap 23 extends over one part of the buckle and then is doubled over onto itself to provide attachment by interconnection of the VELCRO stripping. Similarly, the second strap 25 is extended over the foot and threaded into the buckle, pulled tight against the front, upper surface of the foot, and then secured not only by operation of the buckle but by doubling the VELCRO stripping over onto itself to utilize the interconnection thereof. It has been found preferable to attach the straps 23 and 25 relatively low on the side portions, particularly the inner strap 25 being attached adjacent the heel portion of the stirrup. This causes the straps, when used, to pull the foot and ankle down tight against the heel portion 14.

Means are also provided for securing the padded members to the lower leg of the wearer of the brace. In the preferred embodiment there is include a pair of VELCRO straps which extend between the inner and outer padded members along both the front and back, thereby encircling the person's leg and securing the padded members thereto. As shown, there is included a lower strap 27 and an upper strap 28, each of which is attached to the padded members in the same fashion.

Upper strap 28 is secured at one end to the inner padded member 12 by means of a rivet 29. The exposed surface 30 at this end of the strap 28 has a VELCRO surface. The back side of the strap is a cloth-like surface designed for connection with the VELCRO strip. On the outer padded member 13 there is provided a strip 31 secured to the padded member by a pair of rivets, such as 32. The strip 31 has an exposed VELCRO surface.

To secure the upper strap about the padded members, the strap is pulled around the back of the leg and first attached by connection of the backside of the strap to the exposed VELCRO strip 31. The strap 28 is then pulled around the front of the leg and attached by connection of the backside 33 to the exposed VELCRO strip surface 30. In this manner, the straps 27 and 28 can be used to support the padded members on the leg and in particular permit the location of the padded members and the pressure applied at the front and back sides to be varied to the extent desired.

Figure 3:
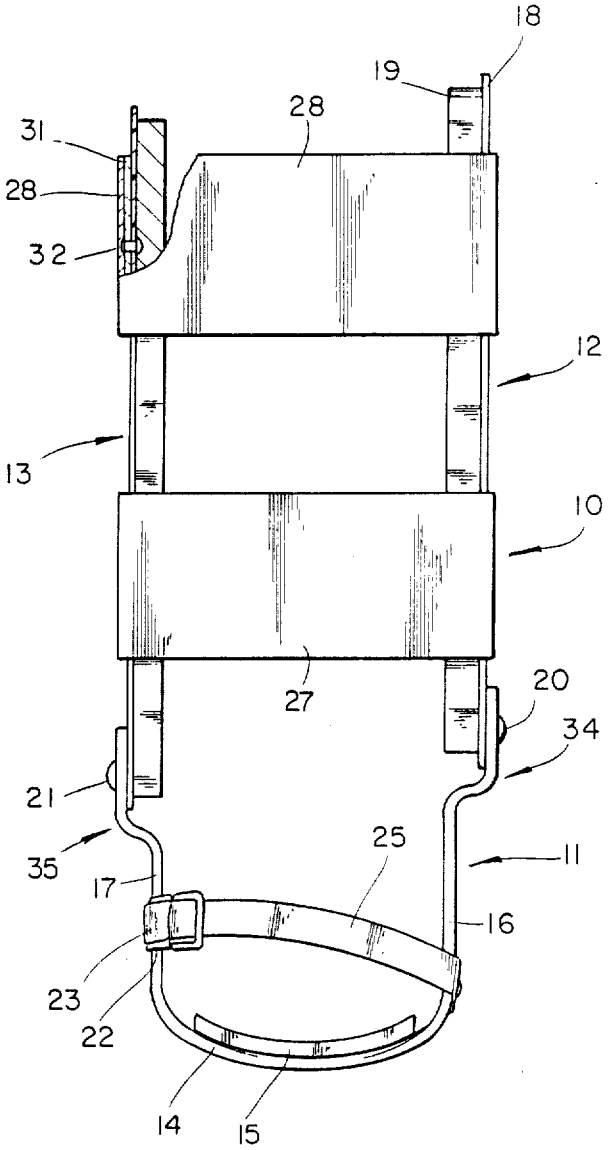
FIG. 3 is a front, elevational view of the ankle brace of FIG. 1, and further including a portion being broken away to show the manner of attachment of the upper strap.

The stirrup can be formed of a variety of materials. However, it is desirable that the stirrup by a substantially rigid member. This permits the ankle brace to support an amount of the downward forces applied to the ankle during walking, running or standing. The stirrup is also preferably configured to fit comfortably over the foot and ankle. As shown particularly in FIG. 3, it is preferable to form the stirrup with the side members displaced outwardly adjacent the upper ends, as shown at 34 and 35. The inner and outer side portions 16 and 17 are connected to the padded members on the outside of the padded members. In this manner, the stirrup is configured in a manner which permits it to be readily received within the person's footwear. A further feature of the design of the heel stirrup is that the heel portion preferably extends forwardly on the outer side 36 to underly the outer portion of the person's foot for providing additional support to the foot and ankle against inversion sprains which are the number one occurring ankle injury.

As described, the present invention is useful in connection with the ankle to immobilize the ankle against inversion and eversion while permitting plantoflexion and dorsiflexion. The unit is anatomically correct with the axes of pivoting being place directly over the medial and lateral malleolous. This placement of the axes reduces component failure, and provides for free and proper movement of the ankle while the brace is being worn. This apparatus thereby provides a high degree of bracing for an individual's ankle while permitting desired motion. The device is light in weight, is not bulky, and is relatively inexpensive.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What I claim is:

1. An ankle brace apparatus for restricting inversion and eversion while permitting plantoflexion and dorsiflexion, said apparatus comprising:

a substantially rigid heel stirrup having a heel portion and a pair of upstanding inner and outer side portions, the heel portion and side portions being configured to be received about a person's foot with the side portions extending upwardly along opposite sides of the foot and overlying the ankle bones;

an inner padded member pivotally connected with the inner side portion of said heel stirrup and configured to be received adjacent the inside of the lower portion of the person's leg, said inner padded member including a substantially rigid support member and padding mounted to the support member and facing the person's leg;

an outer padded member pivotally connected with the outer side portion of said heel stirrup and configured to be received and adjacent the outside of the lower portion of the person's leg, said outer padded member including a substantially rigid support member and padding mounted to the support member and facing the person's leg;

first connection means for pivotally connecting the inner padded member with the inner side portion of said stirrup with a first pivotal axis located adjacent and extending through the person's inner ankle bone;

second connection means for pivotally connecting the outer padded member with the outer side portion of said stirrup with a second pivotal axis located adjacent and extending through the person's outer ankle bone, the [first] *second* pivotal axis being spaced closer than the [second] *first* pivotal axis to the heel portion of said heel stirrup;

first attachment means for attaching said heel stirrup to the person's foot, said first attachment means including strap means for connection to each of the side portions and for being secured together overlying the front, upper surface of the person's foot; and second attachment means for attaching said inner and outer padded members to the person's leg with the padding resting against the inner and outer portions, respectively, of the lower leg.

2. The apparatus of claim 1 in which said heel stirrup includes a padding member mounted to the upper surface of the heel portion.

3. The apparatus of claim 1 in which the heel portion of said heel stirrup extends forwardly on the outer side to underly the outer portion of the person's foot.

4. The apparatus of claim 1 in which said first attachment means comprises a VELCRO strap connectable between the inner and outer side portions.

5. The apparatus of claim 1 in which said second attachment means comprises a pair of VELCRO straps extending between the inner and outer padded members along both the front and back, thereby encircling the person's leg and securing said padded members thereto.

6. The apparatus of claim 5 in which said first attachment means comprises a VELCRO strap connectable between the inner and outer side portions.

7. The apparatus of claim 1 in which said first and second connection means comprises rivots connecting said inner and outer padded members with the inner and outer side portions, respectively.

8. The apparatus of claim 7 in which the inner and outer side portions are connected to said padded members on the outside of said padded members.

9. The apparatus of claim 7 in which the first attachment means comprises a VELCRO strap connectable between the inner and outer side portions.

10. The apparatus of claim 7 in which said second attachment means comprises a pair of VELCRO straps extending between the inner and outer padded members along both the front and back, thereby encircling the person's leg and securing said padded members thereto.

11. The apparatus of claim 10 in which said first attachment means comprises a VELCRO strap connectable between the inner and outer side portions.

12. The apparatus of claim 11 in which said heel stirrup includes a padding member mounted to the upper surface of the heel portion.

13. The apparatus of claim 12 in which the heel portion of said heel stirrup extends forwardly on the outer side to underly the outer portion of the person's foot.

14. The apparatus of claim 1 in which the [first] *second* pivotal axis is spaced closer than the [second] *first* pivotal axis to the heel portion by a distance equal to the horizontal distance between the inner and outer ankle bones.

* * * * *